United States Patent [19]

Caviezel et al.

[11] Patent Number: 5,185,336
[45] Date of Patent: Feb. 9, 1993

[54] METHOD FOR PRODUCING SUBSTANTIALLY PURE VITAMIN POWDERS

[75] Inventors: Gerold Caviezel, Münchenstein; Frank Mertin, Magden, both of Switzerland; Jean-Claude Tritsch, St. Louis, France

[73] Assignee: Hoffmann-La Roche Inc., Nutley, N.J.

[21] Appl. No.: 823,214

[22] Filed: Jan. 21, 1992

[30] Foreign Application Priority Data

Jan. 28, 1991 [CH] Switzerland ............................ 250/91
Nov. 20, 1991 [CH] Switzerland .......................... 3402/91

[51] Int. Cl.⁵ .................. A61K 31/525; A61K 31/51; A61K 31/44; A61K 31/34
[52] U.S. Cl. .................................... 514/251; 514/276; 514/345; 514/474; 514/951
[58] Field of Search ............... 514/276, 251, 345, 474, 514/951

[56] References Cited

U.S. PATENT DOCUMENTS

| | | | |
|---|---|---|---|
| 3,293,132 | 12/1966 | Stoyle et al. | 514/474 |
| 3,396,226 | 8/1968 | Cavalli et al. | 514/474 |
| 4,454,125 | 6/1984 | Demopoulos | 514/474 |
| 4,486,435 | 12/1984 | Schmidt et al. | 514/474 |
| 4,533,674 | 8/1985 | Schmidt et al. | 514/474 |
| 4,605,666 | 8/1986 | Schmidt et al. | 514/474 |
| 4,977,190 | 12/1990 | Meyer et al. | 514/951 |
| 5,000,888 | 3/1991 | Kilbride et al. | 264/7 |
| 5,064,829 | 11/1991 | Izuhara et al. | 514/251 |
| 5,120,762 | 6/1992 | Hanaoka et al. | 514/474 |

FOREIGN PATENT DOCUMENTS

85/01877 5/1985 PCT Int'l Appl. .

OTHER PUBLICATIONS

Derwent Abstract of 85/01877 World No. 85-122406/20.

*Primary Examiner*—Frederick E. Waddell
*Assistant Examiner*—Raymond J. Henley, III
*Attorney, Agent, or Firm*—George M. Gould; George W. Johnston; Stephen L. Malaska

[57] ABSTRACT

A process for the production of free-flowing, directly compressible, at least 99.5% by weight pure vitamin $B_1$, vitamin $B_2$, vitamin $B_6$, vitamin C, sodium ascorbate or calcium ascorbate comprises spray drying a 5 to 25% aqueous solution or suspension of the corresponding vitamin or sodium or calcium ascorbate. The products of this process as well as tablets and other solid dosage forms, which can be formed from these products, are also described.

15 Claims, No Drawings

METHOD FOR PRODUCING SUBSTANTIALLY PURE VITAMIN POWDERS

FIELD OF THE INVENTION

The present invention is concerned with the production of a free-flowing, substantially pure form of vitamin $B_1$, $B_2$, $B_6$ or C or of sodium ascorbate or calcium ascorbate, which form subsequently, and as required, can be compressed directly into tablets or other solid dosage forms or can be converted into mixed formulations using desired adjuvants.

BACKGROUND

Efforts have been made for a long time to produce pure, directly compressible forms of vitamin C and other vitamins on a commercial scale, although without great success. Most of the known commercially obtainable, direclty compressible vitamin forms contain at least 2% of adjuvants. The presence of the adjuvants aid the flowability and compressibility of the powders and the hardness, friability resistance, disintegration time and stability against decolorization of the compressed forms, e.g. tablets, including effervescent tablets, cores etc. The water insolubility, and thus, the sedimentation, of certain adjuvants during the dissolution of the vitamin in water is a great disadvantage.

A known method for the production of vitamin powders, which necessarily contain small amounts of adjuvants, comprises spray drying an aqueous suspension of the vitamin, for example, vitamin C, and the adjuvants such as carbohydrates and film-forming hydrophilic, organic colloidal materials, for example, gelatine, water-soluble casein derivatives, water-soluble resins or water-soluble cellulose derivatives. However, the thus-obtained powder is not directly compressible and must be mixed with a lubricant before it becomes a directly compressible form. Such a method is described, for example, in U.S. Pat. No. 3,293,132.

An additional method for the production of directly compressible vitamin powders is described in U.S. Pat. No. 3,396,226. In that patent, a vitamin C powder is prepared by mixing vitamin C and microcrystalline cellulose, in the presence of a lubricant, especially titanium dioxide or magnesium stearate, before it can be compressed into tablets and the like.

A further known method for the production of directly compressible vitamin powders is known from U.S. Pat. No. 4,533,674. Here, a vitamin C powder is prepared by spray drying an aqueous suspension of vitamin C and a binding agent, e.g. microcrystalline cellulose, in the presence of an absorbent, especially silicon dioxide. In this case also a lubricant, e.g. magnesium stearate, must be added to the thus-prepared vitamin powder before it can be compressed into tablets and the like.

Another method is described in PCT Application No. PCT/US 84/01694 (Publication No. WO 85/01877) in which the lubricant is not mixed subsequently with the vitamin powder, but is admixed during the spray drying process or is already present in the aqueous suspension which contains vitamin C, a binder, and a lubricant.

The above known methods are, however, rather complicated, as pre-mixing steps and in some instances also post-mixing steps are required. Further, immediately after spray drying, the methods lead to vitamin powders which necessarily contain a substantial amount of adjuvants. The present invention largely solves these problems and is a simplification of the production methods hitherto used.

SUMMARY OF THE INVENTION

The present invention pertains to a process for the production of free-flowing, directly compressible, compositions of at least 99.5% by weight of vitamin $B_1$, vitamin $B_2$, vitamin $B_6$, vitamin C (ascorbic acid), sodium ascorbate or calcium ascorbate. The process comprises spray drying a 5 to 25% aqueous solution or suspension of the corresponding vitamin or sodium or calcium ascorbate.

DETAILED DESCRIPTION OF THE INVENTION

By the process in accordance with the invention the physical form of the starting material, i.e. the vitamin $B_1$, $B_2$, $B_6$, C or sodium or calcium ascorbate, is altered such that the product has, inter alia, substantially improved compressibility properties. Moreover, the product is obtained in substantially pure, form, i.e. the use of adjuvants in the spray drying process is superfluous. The degree of purity is at least 99.5%, in most instances even 99.7 to 100%. The product is directly compressible and the conventional complicated granulate production, large and fine sieving, intermediate drying and mixing, which are associated with the expenditure of a large amount of energy and time as well as solvent problems, are not necessary.

The process in accordance with the invention is carried out by spraying an aqueous solution or suspension of the starting material of appropriate concentration into a spray drying tower, conveniently in a manner known per se. Not only static single component or two component nozzles, but also rotary nozzles are suitable for atomizing the solution or suspension during its introduction into the tower. A rapid evaporation of the solvent or suspension medium (water) takes place in the tower, which can be expedited by the simultaneous introduction of hot air. This air can be introduced either in parallel flow or in countercurrent flow. The fine powder which results is partly collected in the lower region of the tower (the "tower material") and is partly drawn off with the spent air into a laterally arranged cyclone and collected there on a filter (the "cyclone material"). The properties of the tower material and of the cyclone material can differ somewhat from each other, but both materials have a good compressibility.

The concentration of the aqueous solution or suspension of the starting material is generally, depending on the solubility or suspendibility limit, 5 to 25% (weight percent), preferably 5 to 12% and especially about 10%. Conveniently, this solution or suspension is introduced at room temperature (about 15° C. to 25° C.) into the spray drying tower. Depending on the solubility or suspendibility and stability of the starting material, the desired concentration of the solution or suspension as well as technical specifications of the spray arrangement, the solution or suspension can, however, be heated to about 80° C. before it is sprayed in. The temperature of the solution or suspension which is sprayed in is preferably room temperature.

The temperature of the hot air ("supply air") which is simultaneously introduced is preferably 120° C. to 200° C., especially about 130° C. to 150° C. The velocity at which the supply air is introduced also influences the quality (compressibility etc.) of the product. The optimal velocity depends on many factors such as, for example, the velocity at which the solution or suspension of the starting material is introduced, the other features of the spraying (degree of atomization, stream geometry etc.) and the volume and the geometry of the spray drying tower, and can therefore not generally be quantified. It can be determined on a case to case basis by a person skilled in the art.

When rotating atomization systems (rotating nozzles) are used, the speed at which the nozzles are rotated plays a role with respect to the quality of the product. As in the case of the optimal velocity at which the supply air is introduced (see above), this rotation speed depends on various factors. In this instance also it can be determined on a case to case basis by a person skilled in the art. When static single component nozzles (also known as pressure spray nozzles), in which the atomization is brought about by hydraulic pressure, are used to spray in the solution or suspension of the starting material, the pressure under which the solution or suspension is sprayed into the spray drying tower is suitably 10 to 100 kg/cm$^2$ ($9.8067 \times 10^5$ to $9.8067 \times 10^6$ Pa). When static two component nozzles are used, in which the atomization is brought about by kinetic energy, this pressure is suitably 2 to 10 kg/cm$^2$ ($1.9613 \times 10^5$ to $9.8067 \times 10^5$ Pa). The solution or suspension and supply air are sprayed into the tower simultaneously using the latter nozzles.

All of the aforementioned parameters, i.e. the concentration of the solution or suspension in the range of 5 to 25 weight percent which is used, its temperature and pressure when sprayed in, the temperature of the supply air, the velocity at which it is introduced, the type of nozzle arrangement, the volume and geometry of the spray drying tower etc., influence the quality of the vitamin powder produced in accordance with the invention and stand in a dependent relationship to one another. The optimal relationship can be determined by a person skilled in the art.

The aforementioned vitamins can be used in the process in accordance with the invention not only as such, but also in the form of their usual salts. When vitamin B$_1$ is used in the process in accordance with the invention, this is used most preferably in the form of its hydrochloride salt or nitrate salt. Vitamin B$_2$ is preferably used as riboflavin itself or as riboflavin phosphate sodium salt and vitamin B$_6$ is preferably used as pyridoxine hydrochloride or pyridoxal phosphate. The corresponding forms are converted using the process in accordance with the invention into a free-flowing, directly compressible form which is at least 99.5% pure.

The process in accordance with the invention is however preferably suited to the production of free-flowing, directly compressible at least 99.5% by weight pure pyridoxine hydrochloride, vitamin C or sodium ascorbate, especially vitamin C.

After the spray drying has been carried out, the product, irrespective of whether it is tower or cyclone material, can be further processed, especially directly compressed in a conventional manner into tablets or other solid administration forms. This can be carried out with the tower material, with the cyclone material or with a mixture of the two products in any desired ratio. If desired, however, any small amounts of one or more adjuvants, e.g. a lubricant, can be admixed as a pre-stage in order to confer particular properties, e.g. still greater hardness, friability resistance, disintegration time, stability etc, to the subsequently manufactured tablets and the like. As the product of the process in accordance with the invention is an almost pure or one hundred percent pure vitamin powder the final composition after the addition of adjuvants can be determined at will in order to determine the desired properties more easily than before. Likewise, different products prepared in accordance with the invention can be mixed with one another in order to obtain mixed vitamin formulations.

The present invention is also concerned with a free-flowing, at least 99.5% pure form of vitamin B$_1$, B$_2$, B$_6$ or C or of sodium or calcium ascorbate produced in accordance with the invention and with tablets and other solid administration forms, which are formed by compression from such a free-flowing form of the above vitamin or sodium or calcium ascorbate or from a mixture of one or more thereof.

The following examples are illustrative of the invention.

EXAMPLE 1

An aqueous solution of pure vitamin C with a concentration of 5, 10 or 15% (weight percent) is sprayed at room temperature into a spray drying tower using rotation nozzles (about 23,000 revolutions/min.). Hot air at 130°–170° C. is simultaneously introduced into the tower at a velocity of 1000–2000 m$^3$/hour.

The resulting spray-dried vitamin C powder is collected partly in the lower region of the tower and partly in the laterally arranged cyclone of the tower. The corresponding tower and cyclone material is removed and its moisture (water content) and particle size are measured in a conventional manner. Its stability against coloration is also investigated.

Each material is then mixed with modified starch (Sta-Rx 1500) and lubricant (magnesium stearate) in order to provide a composition consisting of 90.90, 7.6 and, respectively, 1.5 weight percent of the three components. The composition is subsequently compressed under a pressure force of 2500 KP (Kilopounds = $1.134 \times 10^5$ kg) into 500 mg vitamin C tablets and these are evaluated for hardness, friability resistance and disintegration time (in water at 37° C.). The standard deviation of the tablet weight is also measured.

Both the tower material and the cyclone material exhibit an extremely low moisture (less than 0.5% water content) and a good stability against coloration. The other results of the various aforementioned measurements and investigations are compiled in the Table 1 hereinafter:

TABLE 1

| | Tower material | Cyclone material |
|---|---|---|
| a) 5% vitamin C solution | | |
| Spray-dried powder:- | | |
| Particle size distribution | 92–220 μm | 32–124 μm |
| Average particle size | 129 μm | 66 μm |
| 500 mg vitamin C tablets | | |
| Hardness | 124N | 121N |
| Friability resistance | 0.72% | 0.54% |
| Standard tablet weight deviation | 0.38% | 1.05% |
| Disintegration time (in water at 37° C.) | 55 sec. | 45 sec. |
| b) 10% vitamin C solution | | |
| Spray-dried powder:- | | |
| Particle size distribution | 100–297 μm | 30–142 μm |
| Average particle size | 160 μm | 75 μm |
| 500 mg vitamin C tablets:- | | |
| Hardness | 120N | 119N |
| Friability resistance | 1.76% | 0.18% |

TABLE 1-continued

| | Tower material | Cyclone material |
|---|---|---|
| Standard tablet weight deviation | 0.58% | 1.49% |
| Disintegration time (in water at 37° C.) | 65 sec. | 65 sec. |
| c) 15% vitamin C solution Spray-dried powder:- | | |
| Particle size distribution | 120-291 μm | 38-167 μm |
| Average particle size | 170 μm | 88 μm |
| 500 mg vitamin C tablets:- | | |
| Hardness | 68N | 110N |
| Standard tablet weight deviation | 0.66% | 0.51% |
| Disintegration time (in water at 37° C.) | 50 sec. | 60 sec. |

EXAMPLE 2

An aqueous solution of pure sodium ascorbate with a concentration of 10% (weight percent) is sprayed at room temperature into a spray drying tower using rotation nozzles (about 23,000 revolutions/min.). Hot air at 130° C. (supply air) is simultaneously introduced into the tower at a velocity of 2,000 m³/hour. The temperature of the exhaust air is 105° C.

The resulting spray-dried sodium ascorbate powder is collected partly in the lower region of the tower and partly in the laterally arranged cyclone of the tower. The corresponding tower material and cyclone material are removed.

Each material as well as standard sodium ascorbate granulate USP (a material of United States Pharmacopoeia quality) is mixed individually with ascorbic acid 98% DC, sugar DC (White Di-Pac ®), corn starch, Aspartame ® and magnesium sulphate to give a composition as set forth in Table 2a hereinafter:

TABLE 2a

| Composition | Standard | Tower material | Cyclone material |
|---|---|---|---|
| Ascorbic acid 98% DC (1) | 130.1 mg | 130.1 mg | 130.1 mg |
| Sodium ascorbate granulate USP | 143.5 mg | — | — |
| Sodium ascorbate 100% DC tower (1) | — | 143.5 mg | — |
| Sodium ascorbate 100% DC cyclone (1) | — | — | 143.5 mg |
| Sugar DC (1) [White Di-Pac ® (2)] | 295.0 mg | 295.0 mg | 295.0 mg |
| Corn starch | 43.9 mg | 43.9 mg | 43.9 mg |
| Aspartame ® (3) | 1.5 mg | 1.5 mg | 1.5 mg |
| Magnesium stearate | 6.0 mg | 6.0 mg | 6.0 mg |
| | 620.0 mg | 620.0 mg | 620.0 mg |

(1) DC signifies direct compressible
(2) White Di-Pac ® is a commercially obtainable sugar (Amstar, USA)
(3) Aspartame ® is L-aspartyl-L-phenylalanine methyl ester, a potential sweetener developed by Ajinimomoto and Searle having 140 times greater sweetening power than saccharose.

Then, each composition is compressed under a force of 2000 KP to sodium ascorbate tablets and these are tested for hardness and friability resistance. In addition, the standard tablet weight deviation is measured in each case. The results are compiled in Table 2b hereinafter:

TABLE 2b

| Sodium ascorbate tablets | Standard | Tower material | Cyclone material |
|---|---|---|---|
| Hardness | 83N | 135N | 156N |
| Friability resistance | — | 0.80% | 0.48% |
| Standard tablet weight deviation | 0.24% | 0.41% | 0.35% |

EXAMPLE 3

The following standard, tower material and cyclone material compositions are produced analogously to the procedure described in Example 2 using vitamin $B_6$ hydrochloride in place of sodium ascorbate:

TABLE 3a

| Composition | Standard | Tower material | Cyclone material |
|---|---|---|---|
| Vitamin $B_6$ HCl DC 98% (1) | 443.48 mg | — | — |
| Vitamin $B_6$ HCl 100% DC tower (1) | — | 443.48 mg | — |
| Vitamin $B_6$ HCl 100% DC cyclone (1) | — | — | 443.48 mg |
| Avicel ® PH 102 (4) | 51.30 mg | 51.30 mg | 51.30 mg |
| Magnesium stearate | 5.22 mg | 5.22 mg | 5.22 mg |
| | 500.0 mg | 500.0 mg | 500.0 mg |

(1) see Example 2
(4) Avicel ® is microcrystalline cellulose (FMC Corp., USA). The "PH" products are used as fillers, binders, fluidizers, dispersants and carriers, especially in tabletting in the pharmaceutical industry.

Then, each composition is compressed under a force of 1000 KP to vitamin $B_6$ hydrochloride tablets and these are tested for hardness and friability resistance. The results are compiled in Table 3b hereinafter:

TABLE 3b

| Vitamin $B_6$ hydrochloride | Standard | Tower material | Cyclone material |
|---|---|---|---|
| Hardness | 56N | 91N | 82N |
| Friability resistance | — | 0.80% | 0.25% |

What is claimed is:

1. A process for producing a free-flowing powder comprising at least 99.5% by weight of a compound selected from the group consisting of vitamin $B_1$, vitamin $B_2$, vitamin $B_6$, vitamin C, sodium ascorbate, calcium ascorbate, and the pharmaceutically acceptable salts thereof; said process comprising preparing an aqueous solution or suspension consisting essentially of water and approximately 5% to 25% by weight of said compound, and spray drying said solution or suspension to produce said free-flowing powder.

2. The process according to claim 1, wherein said compound is selected from the group consisting of vitamin $B_1$ hydrochloride, vitamin $B_1$ nitrate, riboflavin phosphate sodium salt, pyridoxine hydrochloride or pyridoxal phosphate.

3. The process according to claim 1, wherein said free-flowing powder has an average particle size of approximately 66 μm to approximately 170 μm.

4. The process according to claim 1, wherein the compound is vitamin C.

5. The process according to claim 1, wherein the compound is sodium ascorbate.

6. The process according to claim 1, further comprising the steps of admixing with said spray dried powder a lubricating amount of a lubricant.

7. The process according to claim 6, wherein said lubricant is magnesium stearate.

8. A process for producing a free-flowing powder consisting essentially of at least 99.5% by weight of a compound selected from the group consisting of vitamin $B_1$, vitamin $B_2$, vitamin $B_6$, vitamin C, sodium ascorbate, calcium ascorbate, and the pharmaceutically acceptable salts thereof; said process comprising preparing an aqueous solution or suspension consisting essentially of water and approximately 5% to 25% by weight of said compound, and spray drying said solution or suspension to produce said free-flowing powder.

9. A free-flowing powder comprising at least 99.5% of a compound selected from the group consisting of vitamin $B_1$, vitamin $B_2$, vitamin $B_6$, vitamin C, sodium ascorbate, calcium ascorbate, and the pharmaceutically acceptable salts thereof; said powder having been produced by preparing an aqueous solution or suspension consisting essentially of water and approximately 5% to 25% by weight of said compound, and spray drying said solution or suspension to produce said free-flowing powder.

10. The free-flowing powder to claim 9, wherein said compound is selected from the group consisting of vitamin $B_1$ hydrochloride, vitamin $B_1$ nitrate, riboflavin phosphate sodium salt, pyridoxine hydrochloride or pyridoxal phosphate.

11. The free-flowing powder according to claim 9, wherein the compound is vitamin C.

12. The free-flowing powder according to claim 9, wherein the compound is sodium ascorbate.

13. The free-flowing powder according to claim 9 further mixed with a lubricating amount of a lubricant.

14. The free-flowing powder according to claim 13, wherein said lubricant is magnesium stearate.

15. The free-flowing powder according to claim 9, wherein said powder has an average particle size of approximately 66 μm to approximately 170 μm.

* * * * *